United States Patent [19]

Thompson et al.

[11] 4,092,868
[45] June 6, 1978

[54] ULTRASONIC INSPECTION OF PIPELINES

[75] Inventors: Robert B. Thompson; George A. Alers, both of Thousand Oaks; Marion A. Tennison, Camarillo, all of Calif.

[73] Assignee: Rockwell International Corporation, El Segundo, Calif.

[21] Appl. No.: 731,199

[22] Filed: Oct. 12, 1976

[51] Int. Cl.² .......................................... G01N 29/04
[52] U.S. Cl. ........................................ 73/638; 73/643
[58] Field of Search ............. 73/67.7, 67.5 R, 67.8 R, 73/67.8 S, 67.9, 71.5 US

[56] References Cited

U.S. PATENT DOCUMENTS

| | | | |
|---|---|---|---|
| 2,995,925 | 8/1961 | Worlton | 73/67.7 |
| 3,120,120 | 2/1964 | Worlton et al. | 73/67.5 R |
| 3,810,384 | 5/1974 | Evans | 73/67.8 S |
| 3,850,028 | 11/1974 | Thompson et al. | 73/67.5 R |

OTHER PUBLICATIONS diNovi; "Lambwaves: Their Use in Nondestructive Testing;" Argonne National Lab and AEC Report; pp. 1–20, Mar. 1963.
Lockett; "Lamb and Torsional Waves and Their Use in Flaw Detection in Tubes," Ultrasonics, Jan. 1973, pp. 31–37.

*Primary Examiner*—Richard C. Queisser
*Assistant Examiner*—Stephen A. Kreitman
*Attorney, Agent, or Firm*—L. Lee Humphries; Craig O. Malin

[57] ABSTRACT

A method and device which are suitable for the in-place inspection of pipelines are provided. A completely self-contained, mobile inspection station is placed inside a pipeline. The station runs through the pipe and transmits Lamb waves within the pipe wall, receives reflected and transmitted portions of the waves, and records the amplitude and phase of the received waves. The recorded information is analyzed to determine the location and nature of discontinuities in the pipe.

7 Claims, 10 Drawing Figures

U.S.Patent  June 6, 1978  Sheet 1 of 4  4,092,868

ULTRASONIC INSPECTION OF PIPELINES

BACKGROUND OF THE INVENTION

1. Field of the Invention

This invention relates to the field of inspection, and more particularly, to the field of ultrasonic inspection of metals.

2. Description of the Prior Art

Non-destructive test (NDT) methods, such as ultrasonic, X-ray, die penetrant, and magnetic inspection, are highly developed for inspecting parts during manufacture and prior to their use. A more difficult and a less developed art is the in-place inspection of large structural items, such as gas and oil pipelines, during their lifetime of use. These pipelines carry flammable products under high pressure, frequently near populated areas, and it is important that their integrity be assured during their many years of use.

Conventional ultrasonic inspection techniques utilize a narrow beam of longitudinal or transverse type waves which is generated in a transducer outside the part to be inspected. The narrow ultrasonic beam is injected into the part by actual contact of the transducer with the part or by contact with a transmitting medium, such as water, which also contacts the part. These prior art techniques are not suitable for inspecting installed pipelines because of the inaccessibility of the pipe and because of the tremendous areas of pipe which must be scanned by the relatively narrow ultrasonic beam. Additionally, wear of the transducer as it moves along the pipe is a serious problem.

Recently, techniques have been developed for generating an ultrasonic Lamb wave in a metal as described in U.S. Pat. No. 3,850,028, entitled, "Method for Ultrasonic Inspection", by the same inventors as the present disclosure. Unlike the commonly used longitudinal or transverse wave, the Lamb wave fills the entire cross section of the object being inspected and is not just a narrow beam of ultrasonic energy. Thus, it can be used to rapidly inspect large areas.

In prior ultrasonic inspection with Lamb waves, the amplitude and phase of beams reflected from defects in the material are analyzed to determine the size and location of the defects causing the reflection. No use is made of the beam which is transmitted past the defect. Because of the large wavelength of the Lamb wave, the reflected wave cannot clearly resolve the shape of small defects causing the reflection. Neither can the reflected wave detect a generalized or nonlocalized uniform decrease in the thickness of an object. Thus, it is not possible to determine the type of defect and the effect of the defect on the integrity of the material utilizing only reflected waves.

SUMMARY OF THE INVENTION

It is an object of the invention to provide an improved method and apparatus for ultrasonic inspection of metals utilizing ultrasonic Lamb waves.

It is a further object of the invention to obtain a more accurate indication of the size and shape of defects in a metal than can presently be obtained utilizing ultrasonic Lamb waves.

It is a further object of the invention to provide a method and apparatus for evaluating non-uniformities in a metal utilizing ultrasonic Lamb waves transmitted past the defect.

It is a further object of the invention to provide a method and apparatus for evaluating the shape, size, and location of defects and non-uniformities in a metal by the analysis of both ultrasonic Lamb waves transmitted past the defect and ultrasonic Lamb waves reflected from the defect.

It is an object of the invention to provide an improved method for the rapid inspection of pipelines in place utilizing ultrasonic Lamb waves.

According to the invention, ultrasonic Lamb waves are transmitted through a metal object. After traveling a predetermined distance through the object, the transmitted waves are detected and the phase is measured. The measured phase is analyzed to determine the existence of non-uniformities in the object.

In a preferred embodiment, the metal object comprises a pipeline and the Lamb waves are transmitted, received, and recorded by a completely self-contained inspection station which moves through the pipe. The amplitude and phase of both transmitted and reflected Lamb waves are detected and analyzed to determine the type of defects in the pipeline.

These and other objects and features of the present invention will be apparent from the following detailed description, taken with reference to the accompanying drawings.

BRIEF DESCRIPTION OF THE DRAWING(S)

DESCRIPTION OF THE PREFERRED EMBODIMENT

Ultrasonic Lamb waves are guided vibrational modes of a wall of material in which ultrasonic energy is trapped between the boundaries of the object and guided around the object by the large mismatch in mechanical impedance between the wall and the surrounding medium. The physical properties of ultrasonic Lamb wave are described by Viktorov in "Rayleigh and Lamb Waves", Plenum Press, 1967. There are two types or groups of Lamb waves, symmetrical waves and antisymmetrical waves (sometimes called flexural waves). The present invention utilizes ultrasonic Lamb waves which are predominantly antisymmetrical.

Figure 1:
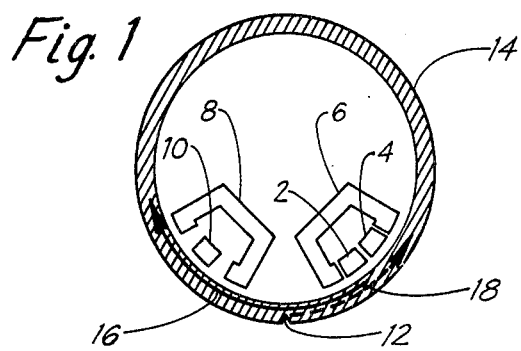
FIG. 1 is a schematic of a cross-section of a pipe with a defect in its wall showing the location and direction of a transmitted wave and a reflected wave with respect to two electromagnets.

Ultrasonic Lamb waves can be transmitted into a metal and received from a metal utilizing alternating current in a coil placed in a static magnetic field as described in U.S. Pat. No. 3,850,028. FIG. 1 shows an arrangement of an ultrasonic Lamb wave transmitted and two receivers for illustrating features of the present invention. A transmitter coil 2 and a receiver coil 4 are positioned between the poles of an electromagnet 6. The magnet 6 can be either an electromagnet or a permanent magnet. Spaced a predetermined circumferential distance from the first magnet 6 is a second magnet 8 with a second receiver coil 10. With this arrangement, a defect 12 in the wall of a pipe 14 between the two magnets can be analyzed by both the transmitted wave 16 coming from transmitter 2 and the reflected wave 18 coming from defect 12. Alternatively, a transmitter and receiver can be positioned longitudinally within the pipe so that the Lamb waves travel longitudinally within the pipe, and transverse non-uniformities such as girth welds can be inspected.

In the embodiment of FIG. 1, the Lamb waves travel circumferentially around the pipe and the circumferential location of a defect in the pipe can be determined by analyzing the phase of the wave reflected by the defect. If the transmitter 2 and receivers 4, 10 are moved longitudinally through the pipe, a plot of the amplitude and phase of both Lamb waves vs. location of the transmitter 2 along the length of the pipe can be obtained.

Figure 2:
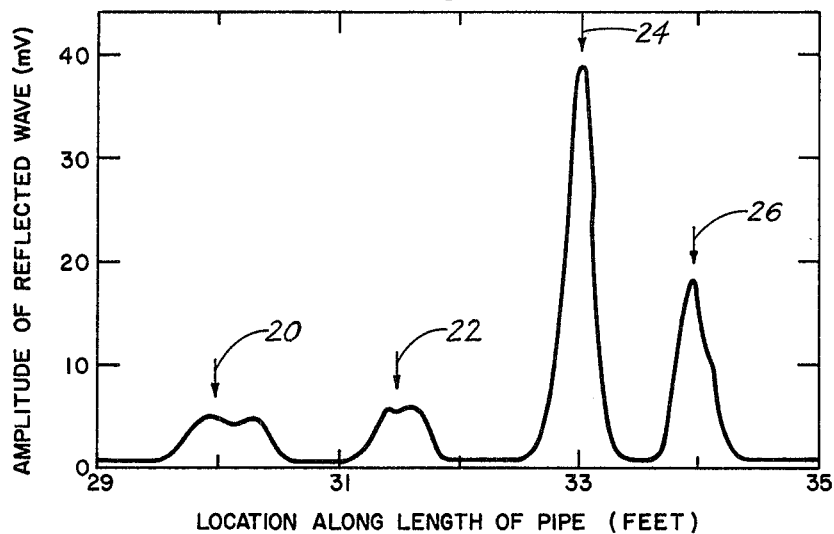
FIG. 2 shows a plot of the amplitude of a Lamb wave reflected from four slots in the wall along a length of pipe.

FIG. 2 is such a plot of the amplitude of the reflected Lamb wave 18 as the apparatus represented by FIG. 1 is moved through the pipe 14. Arrows 20-26 show the location along the length of the pipe of slots machined in the wall of the pipe to simulate longitudinal cracks. Reflected Lamb waves are particularly suitable for indicating the location of sharp discontinuities such as slots or cracks. The circumferential position of the slots in a particular cross section of the pipe can be readily determined by analyzing the phase of the reflected Lamb wave in a manner similar to conventional ultrasonic techniques.

Figure 3:
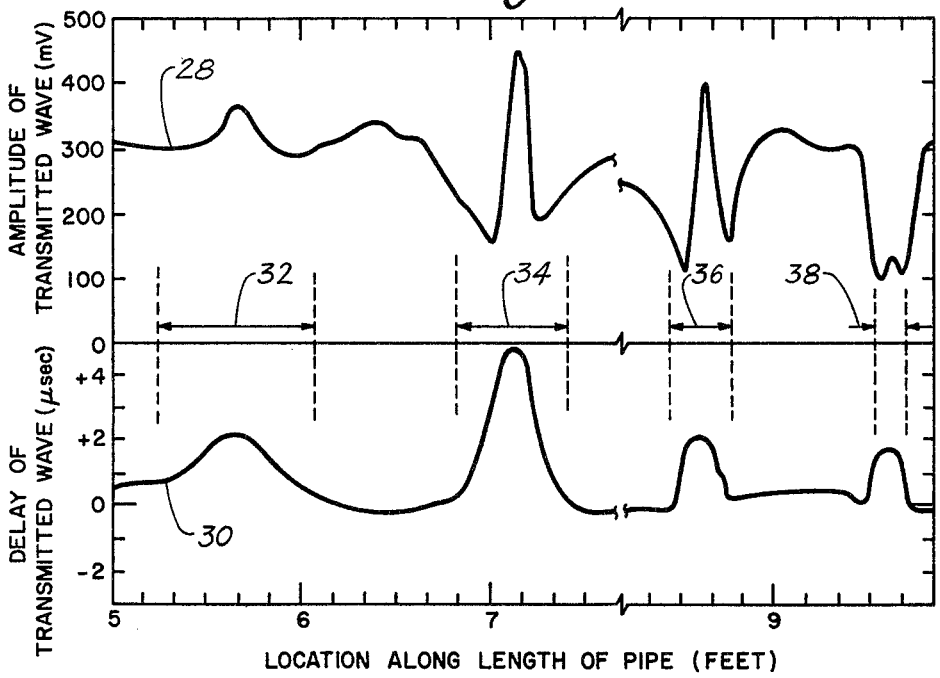
FIG. 3 shows plots of the amplitude and delay of a transmitted Lamb wave caused by four shallow, dish-shaped defects in the wall along a length of pipe.

FIG. 3 shows an amplitude plot 28 and delay plot 30 of the transmitted wave at locations along the length of the pipe. Arrows 32-38 show the location of dish-shaped non-uniformities in the wall of the pipe. These less abrupt discontinuities are typical of thinning or corrosion of the pipe wall and are not readily identified by the usual reflected wave technique. The amplitude and the delay plots of the transmitted wave, however, clearly show their location and extent.

Figure 4:
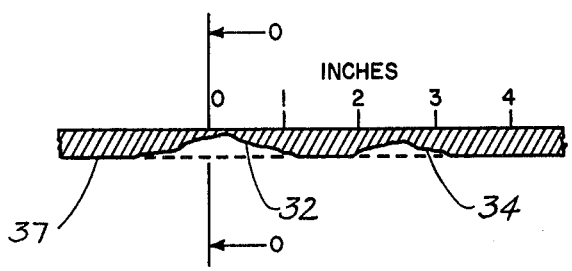
FIG. 4 is a longitudinal section of a pipe through a corroded area.
Figure 5:
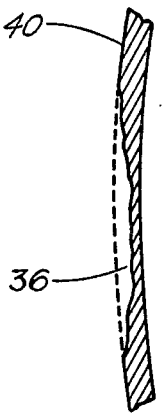
FIG. 5 is a transverse section of pipe through section 0—0 of FIG. 4.
Figure 6:
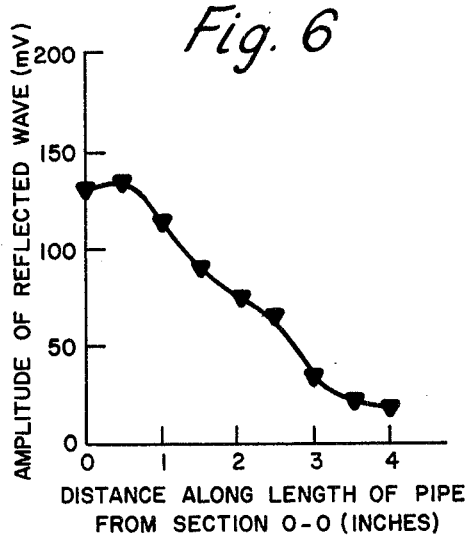
FIG. 6 is a plot of the amplitude of the reflected Lamb wave vs. distance along the pipe from section 0—0 of FIG. 4.

FIGS. 4 and 6 show corroded areas 32-36 in longitudinal and transverse sections respectively on the outside surface 37, 40 of a pipe. The numbers 0-4 show the distances in inches from section 0—0.

Figure 7:
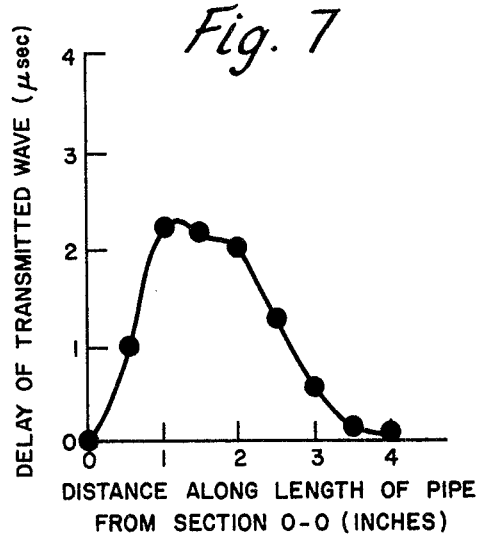
FIG. 7 is a plot of the delay of the transmitted wave vs. distance along the pipe from section 0—0 of FIG. 4.

FIGS. 6 and 7 show the amplitude of the reflected Lamb wave and the delay (phase) of the transmitted Lamb wave for the longitudinal positions shown by the corresponding distances in FIG. 4. The transmitted Lamb wave clearly shows the entire length of the corroded area.

It was discovered that the general shape of the defect or non-uniformity in the pipe could be determined by comparing the amplitude of the reflected wave with the phase or delay of the transmitted wave. To illustrate this correlation, various shaped discontinuities were created in the wall of a pipe which was then inspected utilizing both reflected and transmitted Lamb waves.

Figure 8:
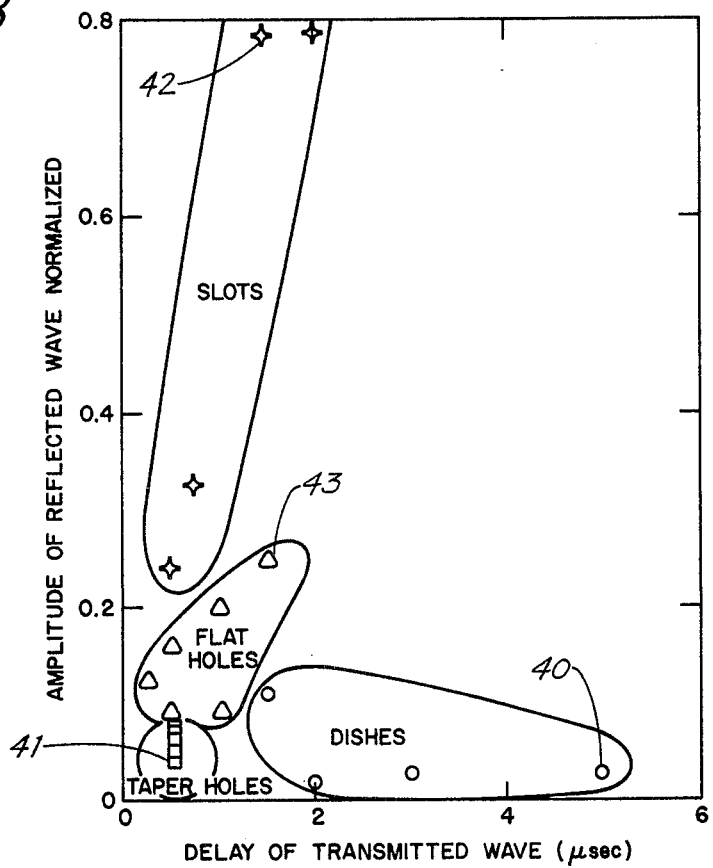
FIG. 8 is a chart of the amplitude of the reflected wave and the delay of the transmitted wave for different types of non-uniformities in the wall of a pipe.

The results are charted in FIG. 8 which shows the delay of the transmitted wave vs. amplitude of the reflected wave (normalized by dividing the reflected amplitude by the round trip amplitude). Defects such as deep dishes 40 that can dangerously reduce the wall thickness of a pressurized pipe return only a small reflected wave and therefore appear harmless based on this single parameter. However, they produce a large delay in the transmitted wave. Conversely, deep slots 42 that can become a likely leak or stress riser in the pipe show only a minor delay in the transmitted wave but have a large reflected amplitude. Tapered holes 41 and flat-bottomed holes 43 can also be distinguished by comparing the reflected and transmitted waves as shown in FIG. 8.

Figure 9:
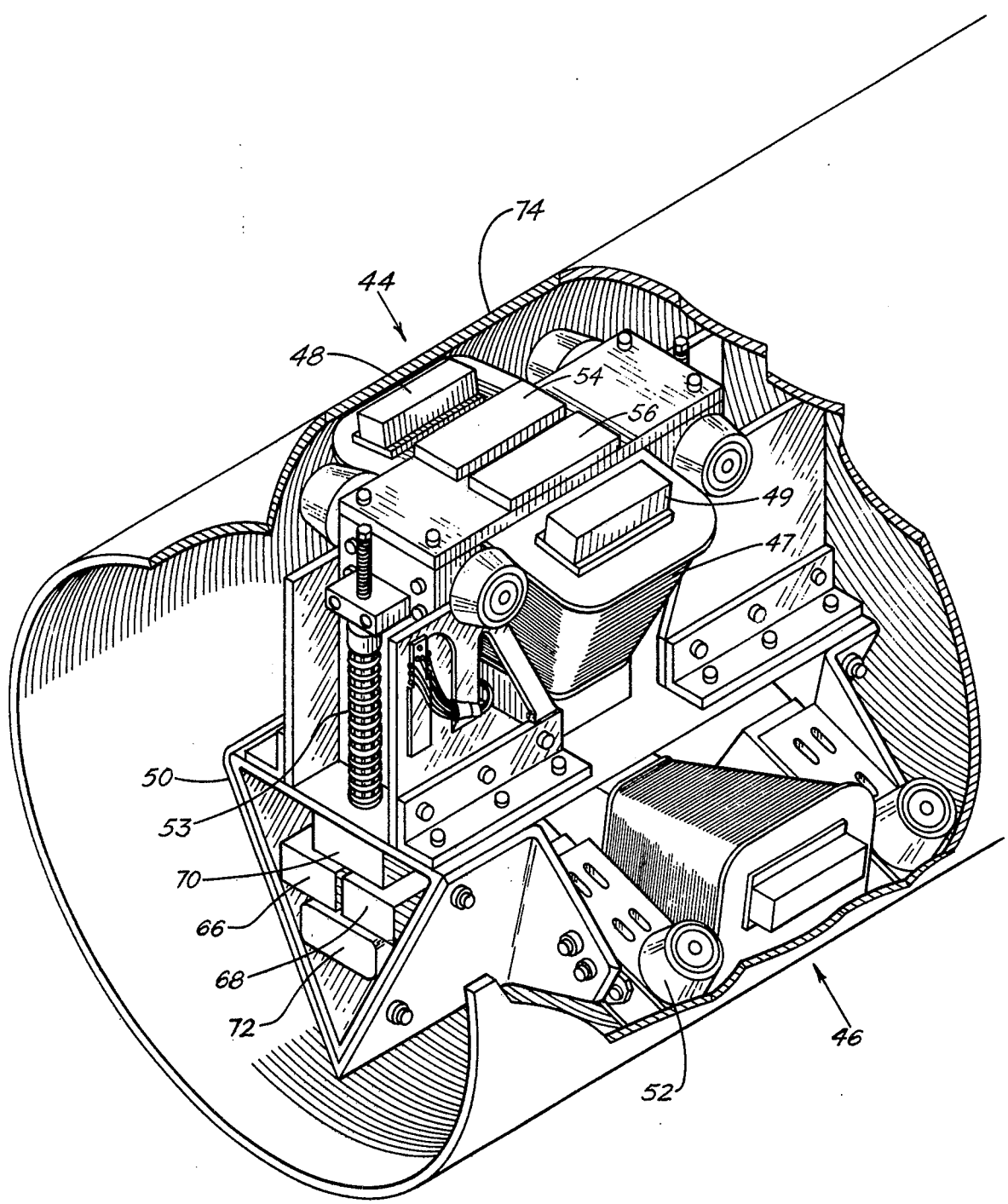
FIG. 9 is a perspective view of an inspection station suitable for practicing the invention.

FIG. 9 is a perspective view of an inspection station according to an embodiment of the invention. Three spaced apart electromagnets 44, 46 (only two being visible in FIG. 9) having poles 48, 49 and windings 47 are supported on a carriage 50 made moveable by wheels 52. A screw adjustment 53 is provided for adjusting at least one pair of wheels against the inside surface of the pipe. Transmitters 54 and receivers 56 (only one each being visible in FIG. 9) are positioned between the poles of the electromagnets. Electronic means 66 for driving the transmitters and electronic means 68 for receiving signals from the receiver are carried on the carriage. A tape recorder 70 and a battery 72 for powering the electromagnets and electronic means are included to make the station completely self-contained. The inspection station fits within a pipe 74 and its cross-sectional surface area is increased by baffles if necessary so that a moving fluid in the pipe line will provide sufficient force to drive the station forward with it.

In a known manner, wire brushes which rub against the inside surface of the pipe can be attached to poles 48, 49 to provide a good flux path to the pipe wall. Also, a second carriage can be provided to carry support equipment such as the battery and electronic gear if the size of the inspection station (required for a particular pipe size) is insufficient.

Figure 10:
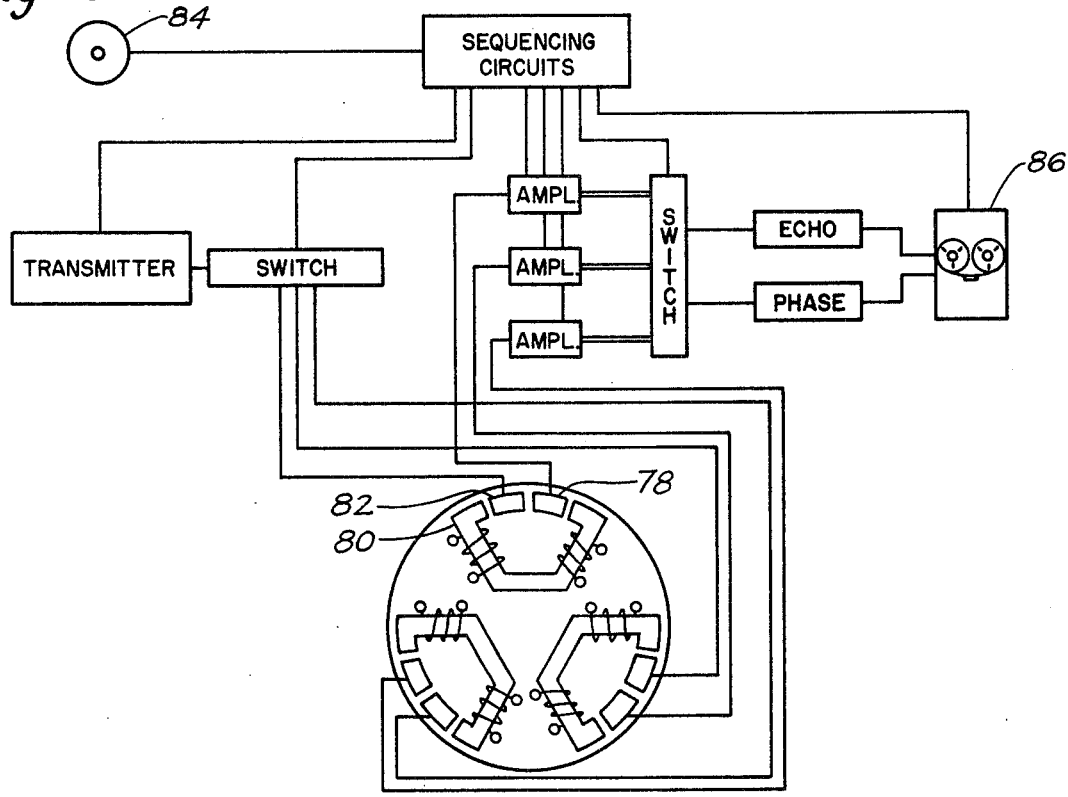
FIG. 10 is a block diagram of an electrical circuit according to an embodiment of the inspection station.

FIG. 10 is a block diagram of an electrical circuit suitable for the inspection station shown in FIG. 9. In order to achieve 360° inspection of the pipe, each transmitter 78 under its corresponding electromagnet 80 is accurately triggered and each receiver 82 correctly switched to the appropriate amplifier by a sequencing and switching network. A distance measuring wheel 84 is included in the circuit so that the location of the station in the pipe is known, and the output of the circuit is recorded by tape recorder 86. When the station is removed from the pipe, the tapes are run through a computer and the results printed out to show the amplitude and phase delay of both the reflected and transmitted wave as a function of the position of the station along the length of pipe being inspected.

Numerous variations and modifications may be made without departing from the present invention. For example, structures other than pipes, such as plates, can be inspected by the method and device of the invention. Additionally, the structure being inspected can be moved adjacent the inspection station rather than move the inspection station along the structure. Accordingly, it should be clearly understood that the form of the present invention described above and shown in the accompanying drawings is illustrative only and is not intended to limit the scope of the present invention.

What is claimed is:

1. An inspection station for a pipe comprising:
   a moveable carriage positionable inside the pipe;
   means for moving said carriage through the pipe;
   a first magnet mounted on said carriage so that the poles of said magnet are spaced apart, close to the inside surface of the pipe when said carriage is positioned within the pipe;
   an ultrasonic Lamb wave transmitter coil and a first receiver coil mounted between said poles;
   a second magnet mounted on said carriage a predetermined distance from said first magnet;
   a second receiver coil mounted between the poles of said second magnet;
   electronic means for driving said transmitter carried by said carriage;
   electronic means for receiving signals from said first and said second receivers carried by said carriage;
   a recorder carried by said carriage and coupled to said electronic receiving means for recording said signals; and
   a battery for powering said electronic driving and receiving means, and said recorder, whereby the portion of the pipe between said first and second magnets can be inspected by ultrasonic Lamb waves reflected by non-uniformities and ultrasonic Lamb waves transmitted past said non-uniformities as said carriage is moved through the pipe.

2. The station as claimed in claim 1, wherein said poles are circumferentially spaced apart and said second magnet is mounted a predetermined circumferential distance from said first magnet, with respect to the pipe.

3. The inspection station as claimed in claim 2, including:
   a second transmitter coil mounted between the poles of said second magnet;
   a third magnet mounted on said carriage a predetermined circumferential distance from said second magnet; and
   a third transmitter coil and a third receiver coil mounted between the poles of said third magnet, whereby 360° of the pipe circumference can be inspected by ultrasonic Lamb waves reflected by discontinuities and transmitted past said discontinuities.

4. The station as claimed in claim 1, wherein said poles are longitudinally spaced apart and said second magnet is mounted a predetermined longitudinal distance from said first magnet, with respect to the pipe.

5. The station as claimed in claim 1, wherein said magnets comprise electromagnets, and said battery powers said electromagnets.

6. An inspection station for a pipe comprising;
   a carriage positionable inside the pipe and occupying sufficient cross-section of the pipe to be moveable by the flow of fluid through the pipe without further locomotion;
   a plurality of electromagnets mounted on said carriage a predetermined circumferential distance apart, the poles of each electromagnet being circumferentially spaced apart close to the inside surface of the pipe when said carriage is positioned within the pipe;
   an ultrasonic Lamb wave transmitter coil and a first receiver coil mounted between said poles of each of said electromagnets;
   electronic means for driving said transmitters carried by said carriage;
   electronic means for receiving signals from said receivers carried by said carriage;
   a recorder carried by said carriage and coupled to said electronic receiving means for recording said signals; and
   a battery for powering said electromagnets, said electronic driving and receiving means, and said recorder, whereby 360° of the circumference of the pipe can be inspected by ultrasonic Lamb waves reflected by non-uniformities and transmitted past said non-uniformities as said carriage is moved through the pipe by the flow of fluid.

7. An inspection station for inspecting an electrically conductive material comprising:
   a station positionable adjacent the material;
   means for moving said station and said material relative to each other;
   a first magnet mounted on said station so that the poles of said magnet are spaced apart, close to the surface of the material when said station is positioned adjacent the material;
   an ultrasonic Lamb wave transmitter coil and a first receiver coil mounted between said poles;
   a second magnet mounted on said station a predetermined distance from said first magnet;
   a second receiver coil mounted between the poles of said second magnet;
   electronic means for driving said transmitter coupled to said transmitter;
   electronic means for receiving signals from said first and said second receivers coupled to said receivers;
   said electronic means including means for measuring the amplitude of said signals from said 1st receiver and the phase of said signals from said 2nd receiver; and
   a battery for powering said electronic driving and receiving means, whereby the portion of the material between said first and second magnets can be inspected by ultrasonic Lamb waves reflected by non-uniformities and ultrasonic Lamb waves transmitted past said non-uniformities as said station and material move relative to each other.

* * * * *